(12) United States Patent
Paufique

(10) Patent No.: US 8,679,556 B2
(45) Date of Patent: Mar. 25, 2014

(54) PROCESS FOR OBTAINING AN ACTIVE INGREDIENT WITH AN IMMEDIATE TENSOR EFFECT ON THE SKIN, ACTIVE INGREDIENT AND COMPOSITIONS

(71) Applicant: Societe Industrielle Limousine D'Application Biologique Dite Silab, Objat (FR)

(72) Inventor: Jean Paufique, Objat (FR)

(73) Assignee: Societe Industrielle Limousine d'Application Biologique (SILAB), Objat (FR)

( * ) Notice: Subject to any disclaimer, the term of this patent is extended or adjusted under 35 U.S.C. 154(b) by 0 days.

(21) Appl. No.: 13/761,443

(22) Filed: Feb. 7, 2013

(65) Prior Publication Data

US 2013/0150322 A1 Jun. 13, 2013

Related U.S. Application Data

(63) Continuation-in-part of application No. 12/442,441, filed as application No. PCT/FR2007/051992 on Sep. 21, 2007, now abandoned.

(30) Foreign Application Priority Data

Sep. 22, 2006 (FR) ...................................... 06 53903
Mar. 8, 2007 (FR) ...................................... 07 53714

(51) Int. Cl.
*A61K 36/899* (2006.01)
*A61K 8/97* (2006.01)
*A61Q 19/00* (2006.01)
*A61Q 19/08* (2006.01)

(52) U.S. Cl.
USPC ........................... 424/750; 424/78.03; 514/23

(58) Field of Classification Search
None
See application file for complete search history.

(56) References Cited

U.S. PATENT DOCUMENTS

| 2003/0147830 A1 | 8/2003 | Phillips et al. |
| 2004/0126449 A1 | 7/2004 | Majmudar et al. |
| 2006/0121131 A1* | 6/2006 | Redmond et al. ............. 424/725 |
| 2006/0263309 A1* | 11/2006 | Bissett ............................. 424/59 |

FOREIGN PATENT DOCUMENTS

| EP | 0 735 049 | 10/1996 |
| FR | 2 838 343 | 10/2003 |
| FR | 2 874 930 | 3/2006 |
| JP | 03-237102 | 10/1991 |
| RU | 2 246 929 | 2/2005 |
| WO | 2005/048735 | 6/2005 |

* cited by examiner

*Primary Examiner* — Chris R Tate
*Assistant Examiner* — Deborah Davis
(74) *Attorney, Agent, or Firm* — Young & Thompson

(57) ABSTRACT

The invention relates to a method for obtaining an active ingredient having an immediate anti-wrinkle and skin-tensioning effect, by extracting and purifying high molecular weight polysaccharides from oat bran, fibers and/or grains, and solubilizing and stabilizing the polysaccharides in water. The invention also relates to the product thus obtained, to uses thereof, and to cosmetic compositions containing this active ingredient. The oat bran polysaccharides include alpha-glucans having a molecular weight of between 25 kDa and 300 kDa.

8 Claims, No Drawings

PROCESS FOR OBTAINING AN ACTIVE INGREDIENT WITH AN IMMEDIATE TENSOR EFFECT ON THE SKIN, ACTIVE INGREDIENT AND COMPOSITIONS

FIELD OF THE INVENTION

This invention relates to a method of providing an immediate anti-wrinkle effect and/or an immediate tensor effect on the skin. The invention also relates to a process for obtaining a polysaccharide-rich active ingredient of high molecular weight that is derived from oat bran, having an immediate anti-wrinkle effect and/or immediate tensor effect on the skin, to the active ingredient that can be obtained by this process, its uses, and the related cosmetic compositions.

BACKGROUND OF THE INVENTION

To appear younger, many people want to tone up their skin and attenuate the directly visible, unsightly physical changes that are linked to cutaneous aging.

The aging of the skin results from various alterations caused by factors that are both genetic and environmental. It manifests itself in particular by the loss of mechanical strength and viscoelastic and lifting properties of the dermis. The skin then has the tendency to stretch under the influence of its own weight, thus causing surface deformations, and the formation of wrinkles and unsightly folds. The epidermis also loses its thickness, and the cutaneous microrelief is modified.

To fight against this phenomenon, cosmetic active ingredients are therefore sought that make it possible both to lift and smooth the cutaneous microrelief, and to improve the viscoelastic properties of the skin at the same time.

To date, to meet their lifting needs, the formulators have had at their disposal two types of substances:
 Synthetic and sticky polymers that are often difficult to formulate because they are only soluble in alcohol, and
 Proteins.

SUMMARY OF THE INVENTION

A purpose of this invention is another molecular means to eliminate the drawbacks of the prior art by proposing a method of providing an immediate anti-wrinkle effect and/or immediate tensor effect on the skin by administering to a subject, oat bran polysaccharide alpha-glucans. The alpha-glucans preferably have a molecular weight of between 25 kDa to 300 kDa.

The invention also relates to a process for obtaining an active ingredient with an immediate tensor effect that is effective, soluble and stable in water, of plant origin, and that limits the protein content as much as possible.

To this end, the invention includes a process for obtaining an active ingredient with an immediate anti-wrinkle effect and/or immediate tensor effect on the skin, characterized in that it consists in extracting and purifying specific polysaccharides of high molecular weight from oat bran and in solubilizing and stabilizing these polysaccharides in water.

The active ingredient according to the invention can be obtained from simple oat fibers and/or from oat bran, residue of the oat grounds obtained from the pericarp of seeds that, in addition to fibers, contains proteins, mineral salts, and vitamins, and/or from oat seeds.

Advantageously, the active ingredient that is obtained, polysaccharide-rich and of a high molecular weight, produces a sensation of stretched and toned skin and has an immediate tensor effect that is characterized by a smoothing of the cutaneous microrelief and an improvement in the mechanical properties of the skin, thus an immediate anti-wrinkle effect.

DETAILED DESCRIPTION OF THE INVENTION

This invention is now described in detail by using non-limiting examples of compositions, as well as test results grouped in tables.

The invention relates to a method of providing an immediate anti-wrinkle effect and/or immediate tensor effect on the skin by administering to a subject in need thereof an effective amount of oat bran polysaccharides of alpha-glucans. Oat bran polysaccharides of alpha-glucans can have a molecular weight of between 25 kDa to 300 kDa.

Preferably the invention relates to a method of providing an immediate anti-wrinkle effect and/or immediate tensor effect on the skin by administering to a subject in need thereof an effective amount of an active ingredient obtained from oat bran containing polysaccharides of alpha-glucans preferably having a molecular weight of between 25 kDa to 300 kDa. Preferably the polysaccharides having a molecular weight of between 25 kDa to 300 kDa represent 90% of the oat bran polysaccharides in the active ingredient.

The invention also relates to a method of providing an immediate anti-wrinkle effect and/or immediate tensor effect on the skin by administering to a subject a cosmetic composition comprising between 1% and 5% by weight of the active ingredient obtained from oat bran containing polysaccharides of alpha-glucans, preferably having a molecular weight of between 25 kDa to 300 kDa.

I/Process for Obtaining the Polysaccharides and the Active Ingredient

The process according to this invention comprises at least two essential stages:
 A stage for solubilization of oat bran and/or fibers and/or seeds in a basic solution, and
 A stage of successive or simultaneous enzymatic hydrolysis(es) of polysaccharides that are contained in the oat bran and/or fibers and/or seeds, so as to facilitate their solubilization without disrupting their molecular structure.

According to an embodiment of the invention, to facilitate the solubilization of polysaccharides, at least one adjuvant for solubilization in the basic solution, preferably a salt, a polyphosphate and/or an oxidizer, is added.

The concentration of alkaline agent of the basic solution for solubilization can be adjusted so that the physical properties of the polysaccharides are not altered by simple sugars during hydrolysis.

Preferably, the process according to this invention also comprises a deproteinization stage.

According to a preferred embodiment, the process according to the invention comprises the series of the following stages:
 Solubilization of an oat bran and/or fibers and/or seeds at a rate of 30 g/l to 300 g/l, more particularly from 50 g/l to 150 g/l, in a basic solution,
 Successive or simultaneous enzymatic hydrolysis(es) of polysaccharides,
 Inactivation by heat or chemical treatment to block the enzymatic reactions,
 Separation of the soluble and insoluble phases by filtration, decanting, and/or centrifuging,
 Successive concentrations,
 Deproteinization by precipitation or selective adsorption, Purification of the active fraction that contains polysaccharide alpha-glucans by ultrafiltration, and Sterilizing filtration.

Advantageously, the process according to the invention allows the preservation of native polysaccharides that are derived from oat bran and/or fibers and/or seeds, while facilitating the industrial feasibility of the active ingredient.

II/Characterization of the Active Ingredient

II.1/Dry Material

The level of dry material is measured by running a sample with a given initial weight through the oven at 105° C. until a constant weight is obtained.

The level of dry material is between 20 and 200 g/l, more particularly between 60 and 110 g/l.

II.2/Measurement of pH

The pH that is measured by the potentiometric method at ambient temperature leads to values of between 4 and 8, more particularly between 5 and 6.

II.3/Determination of the Content of Total Sugars

The method of DUBOIS (DUBOIS, M. et al. (1956), Analytical Chemistry, 28, No. 3, pp. 350-356) is used.

In the presence of concentrated sulfuric acid and phenol, the reducing sugars provide a yellow-orangey compound.

Starting from a standard range, it is possible to determine the level of total sugars of a sample.

The level of total sugars of the active ingredient according to this invention is 19 to 190 g/l, preferably 57 to 105 g/l.

The ratio of the total sugars to the level of dry material for the active ingredient according to this invention is greater than 50%, preferably greater than 80%.

II.4/Mean Polymerization Degree of Polysaccharides

The mean polymerization degree of polysaccharides is determined by the ratio of the level of total sugars to the level of reducing sugars.

The metering of reducing sugars is carried out as follows:

The active ingredient to be metered is brought into the presence of a solution of 4-hydroxybenzoic hydrazide in 0.5 M hydrogen chloride and a 0.5 M soda solution, A standard range is produced with glucose, and The absorbance is measured at 410 nm to determine the content of reducing sugars of the active ingredient relative to the glucose range.

The mean polymerization degree of the polysaccharides of the active ingredient according to this invention is greater than 40, preferably greater than 60.

II.5/Polysaccharide Size

The distribution by size of the polysaccharides that are obtained by the implementation of the process according to the invention is carried out by studying the chromatograms.

The polysaccharides that are obtained by the implementation of the process according to the invention are polysaccharides of high molecular weight. They have a polysaccharide size of between 25 kDa and 700 kDa. Preferably, more than 90% of the polysaccharides have a molecular weight of between 25 kDa to 300 kDa, and preferably these polysaccharides are alpha-glucans.

II.6/Identification of the Molecular Structure of Polysaccharides of the Active Ingredient II.6.1/Main Chain of Glucose in Alpha-1.4 Linkage After specific enzyme action on the alpha-1.4 linkage of the active ingredient according to the invention, two types of compounds were found in the chromatogram: 77% free glucose (molecular weight=180 Da, polymerization degree=1) and 23% oligomeric glucose (molecular weight=666 Da, polymerization degree=4). This mean that 77% of glucose molecules are present in alpha-1.4 linkage.

II.6.2/Main Chain of Glucose Molecules Bound in Alpha-1.6

The action of a mixture of two enzymes (the first specific for the alpha-1.4 linkages between 2 glucose molecules and the second specific for alpha-1.6 linkages) showed that the product is composed of 100% free glucose. This proves the presence of both types of linkages in the active ingredient according to the invention.

II.6.3/Modeling Molecular Structure

According to the preceding data, a structural model of the active ingredient polysaccharides can be made. It was estimated there is one alpha-1.6 linkage every 12 molecules of glucose. Active ingredient polysaccharides are composed of a glucose chain linked by alpha-1.4 linkages, forming a helicoidally structure, ramified by an alpha-1.6 linkage every 12 glucoses, on average.

II.7/Determination of Free Glucose

The free glucose of different samples was determined:

Active ingredient according to the invention.

Active ingredient according to the invention hydrolyzed by acid for 2 hours. This hydrolysis can drastically cut the set of all glucose-glucose links, whatever the nature of the linkage.

Active ingredient according to the invention hydrolyzed by a cellulase enzyme (CELLULYVE® Lyven, France) having a beta-glucanase activity. This hydrolysis allows hydrolyzing only beta linkages between two glucose molecules, thus hydrolyzing beta-glucans exclusively.

The analysis is performed by liquid chromatography ion (Dionex ICS 3000) under the following conditions:

Column: CARBOPAC PA14*250 mm, the pre-column with the same characteristics as the column, Flow rate: 1 ml/min, Solvent:

A: distilled water

B: 100 mM NaOH (sodium ultrapure Fischer, S/4940/17)

C: 100 mM NaOH+500 mM $CH_3COONa$ (VWR PROLABO, RECTAPUR, 27650.292)

| Time (min) | % A | % B | % C |
|---|---|---|---|
| 0 | 80 | 20 | 0 |
| 15 | 80 | 20 | 0 |
| 20 | 80 | 0 | 20 |
| 42 | 50 | 0 | 50 |
| 48 | 50 | 0 | 50 |
| 48 | 0 | 0 | 100 |
| 65 | 0 | 100 | 0 |
| 65 | 80 | 20 | 0 |
| 70 | 80 | 20 | 0 |

Detector: pulsed amperometric,

Oven temperature: 30° C.,

Injection: 25 µl.

The results are as follows:

| Analysed Products | Free glucose content (g/l) |
|---|---|
| Active ingredient according to the invention | 0 |
| Active ingredient hydrolyzed by acid for 2 hours | 72.0 |
| Active ingredient hydrolyzed by beta glucanase | 1.8 |

The results suggest that all the glucose present in the active ingredient according to the invention is in a bound form, since the content of free glucose in the active ingredient is zero and the active ingredient contains 72 g/l of glucose in a bound form, as the content free glucose of the active ingredient completely hydrolyzed is 72 g/l.

The enzyme beta-glucanase can cut glucose links only in beta, and the beta glucanase enzyme frees 1.8 g/l of the 72 g/l of glucose of the active ingredient.

Therefore the active ingredient according to the invention contains 2.5% beta linked glucose, thus 2.5% as beta-glucans.

Because the glucose binds in either beta or alpha, it is concluded that the active ingredient glucose content contains 97.5% of alpha-glucans.

III/Evaluation of the Effect of the Active Ingredient

III-1/Evaluation of the Tensor Effect by Cutometer

This study has as its objective to evaluate the tensor effect of an active ingredient that is obtained according to the invention from oat bran.

The study is performed on volunteers using a Cutometer. A Cutometer is a device that is equipped with a probe that is applied to the skin in which a constant depression is maintained. The depth of penetration of the skin in the probe is measured under the intake effect.

When subjected to these depressions, the skin becomes tired more or less quickly and the response times as well as the measured amplitudes make it possible to determine the parameters, in particular:

An elastic component, Ue, which corresponds to an instantaneous deformation, and Uf, which corresponds to the extensibility.

If Ue decreases, the skin is less flexible and therefore more stretched. If Uf decreases, the skin is less extensible, and therefore also more stretched.

The operating protocol is as follows:

A zone is identified on the volunteers' forearms, and a first series of measurements is taken with the Cutometer, The active ingredient that is derived from oat bran that is obtained according to the invention at 4% in emulsion or a placebo is applied to the identified zone, and Two hours after the application, a new series of measurements is taken on the identified zone.

As reference results, the BSA (bovine serum albumin) metered at 4% is used.

The results that are obtained for the active ingredient that is derived from oat bran according to the invention are expressed relative to the placebo in the table below:

|  | Cosmetic Effectiveness/Placebo | |
| --- | --- | --- |
|  | (ΔUf) | (ΔUe) |
| 4% BSA | −5.0% | −7.1% |
| Active Ingredient According to the Invention | −8.4% | −9.9% |

It is noted that the active ingredient according to the invention reduces the elastic component and the extensibility of the skin: it has an immediate tensor effect on the skin.

III-2/Evaluation of the Tensor Effect in Sensory Analysis

The objective of this study is to quantify in vivo the tensor effectiveness of an active ingredient according to the invention, obtained from oat bran, formulated at 10% of counter-placebo gel.

The sensory evaluation test consists in having a panel of experts make a blind evaluation of the tightening and non-sticky sensation. The study is performed on 15 healthy volunteers at the level of the eye and the crow's-feet.

The operating protocol is as follows:

At T minus 5 minutes, the volunteers remove make-up from the selected eye and crow's-feet, At T 0, 80 µl of a gel that is to be tested is applied: placebo gel, gel that contains 10% of the active ingredient according to the invention that is derived from oat bran, gel that contains 5% BSA, gel that contains 10% BSA, and gel that contains 20% BSA, and At T 3 minutes, T 5 minutes, and T 10 minutes, the tightening sensation is evaluated on a scale of 0 to 10, using a cursor.

The analysis of the scales is carried out by totaling the scores over three cycles.

The various gels are tested randomly over several days (one gel per day).

The results that are obtained are presented in the table below:

|  | Total of the Scores over 3 Cycles |
| --- | --- |
| Placebo | 4.1 |
| Active Ingredient According to the Invention at 10% | 13.6 |
| 5% BSA | 8.2 |
| 10% BSA | 12.9 |
| 20% BSA | 14.6 |

It is noted that after a single application, the experts identify the active ingredient according to the invention as tightening and non-sticky, and score it at an effectiveness of 13.6, which is higher than that of BSA metered at 10%.

III-3/Evaluation of the Immediate Anti-Wrinkle Effect

The object of this study is to quantify the immediate anti-wrinkle effectiveness of an active ingredient according to the invention, obtained from oat seeds, formulated at 4% in counter-placebo emulsion.

The study is performed on healthy female volunteers.

Anti-wrinkle effectiveness is measured by means of silicone imprints made in the crow's-feet of volunteers.

The analysis of these imprints using a profilometer equipped with an image analyzer makes it possible to obtain three parameters: the number of wrinkles, the total wrinkled surface area, and the total length of the wrinkles.

The study is performed according to the following protocol.

At T 0, two symmetrical cutaneous zones are identified at the crow's-feet—one intended to be treated by placebo, the other by the active ingredient—and imprints are made of these two zones.

After the imprints are made, the placebo and the active ingredient according to the invention, derived from oat seeds and formulated at 4%, are applied to the defined zones.

At T 2 hours, the imprints are made on the two zones that are being studied.

The results that are obtained for the active ingredient according to the invention, derived from the oat seeds, are expressed in the table below by percentage relative to those obtained for the placebo:

|  | Variation/Placebo (%) |
| --- | --- |
| Number of Wrinkles | −11.5 |
| Total Wrinkled Surface Area | −17.4 |
| Total Length | −13.9 |

It is noted that after two hours, in comparison to the placebo, the active ingredient according to the invention that is formulated at 4% reduces the number of wrinkles, the total wrinkled surface area, and the total length of the wrinkles at the same time. It therefore has an immediate anti-wrinkle effect.

III-4/Evaluation of the Tensor Effect in Sensory Analysis

The objective of this study is to quantify in vivo the tensor effectiveness of the active ingredient according to the invention, obtained from oat seeds, formulated at 4% of counter-placebo gel.

The sensory evaluation test consists in having a panel of experts make a blind evaluation of the tightening and non-sticky sensation, formed with this tightening sensation. The study is performed on 15 healthy volunteers at the level of the eye and the crow's-feet.

The operating protocol is as follows:
At T minus 5 minutes, the volunteers remove make-up from the selected eye and crow's-feet,
At T0, 80 µl of a gel that is to be tested is applied: a placebo gel or a gel that contains 4% of the active ingredient according to the invention that is derived from oat seeds, and
At T 3 minutes, T 5 minutes, and T 10 minutes, the tensor sensation is evaluated on a score scale that ranges from 0 to 10, using a cursor.

The results that are obtained, corresponding to the mean of the scores with three cycles, are presented in the table below:

|  | Mean Score |
| --- | --- |
| Placebo | 2.1 |
| Active Ingredient According to the Invention at 4% | 4.4 |

It is noted that after a single application, the experts identify the active ingredient according to the invention as tightening and non-sticky, and score it at an effectiveness of 4.4.

IV/Cosmetic Composition Including the Active Ingredient

This invention also covers the cosmetic compositions including the active ingredient according to this invention in various galenical forms, in particular gel, solution, emulsion, cream.

It is then advisable to analyze the stability of the galenical forms, including the active ingredient according to the invention, in proportions of between 1 and 5%. The stability is characterized by an absence of precipitation of the active ingredient, an absence of creaming, and an absence of phase shift.

It is possible to cite formulations that have shown a physical stability that includes 5% of active ingredient according to the invention.

Clear Gel:
  CARBOPOL: 0.5% with triethanolamine—sufficient quantity for pH=6.5
  Preservative: 0.7%
  Active ingredient: 5.0%
  Water: 93.8%
Opaque Gel:
  SEPIGEL 305: 2.0%
  Preservative: 0.7%
  Active ingredient: 5.0%
  Water: 92.3%
Emulsified Gel:
  MONTANOV 202: 3.0%
  Isopropyl palmitate: 12.0%
  Preservative: 0.7%
  VISCOLAM AT 64: 2.0%
  Active ingredient: 5.0%
  Water: 77.3%
Non-Ionic Emulsion:
  MONTANOV 202: 3.0%
  SIMULSOL 165: 2.0%
  Isopropyl palmitate: 20.0%
  Preservative: 0.7%
  Active ingredient: 5.0%
  Water: 69.3%
Anionic Emulsion:
  Stearic acid: 7.0%
  Triethanolamine: 3.5%
  Isopropyl palmitate: 20.0%
  Preservative: 0.7%
  Active ingredient: 5.0%
  Water: 63.8%
Cationic Emulsion:
  Quatemium-82: 5.0%
  Cetyl alcohol: 2.0%
  Cetearyl alcohol: 1%
  PEG100 stearate: 1%
  Isopropyl palmitate: 15.0%
  Preservative: 0.7%
  Active ingredient: 5.0%
  Water: 70.3%

In addition, tests have shown the compatibility of the active ingredient with the raw material used in cosmetics.

EXAMPLES OF COSMETIC FORMULAS

Example 1

Liquid Make-Up Foundation

| | | |
| --- | --- | --- |
| A. | Water | q.s. 100% |
| | DUB DIOL (Stearinerie Dubois) | 6% |
| | Glycerol (Univar) | 4% |
| | Montanox 60 (Seppic) | 0.4% |
| | SATIAXANE CX 930 (Degussa) | 0.2% |
| B. | SIMULSOL 165 (Seppic) | 3% |
| | Rita stearic (Rita) | 2% |
| | Rita CA (Rita) | 1% |
| | DC 345 (Dow Corning) | 3% |
| | DUB Vinyl (Stearinerie Dubois) | 6% |
| | Gemseal 40 (Total) | 7% |
| C. | White W9775(LCW/Sensient) | 7% |
| | Yellow W1771 (LCW/Sensient) | 4.2% |
| | Brown W8770 (LCW/Sensient) | 1.5% |
| | Black W9774 (LCW/Sensient) | 0.5% |
| D. | Phenoxyethanol (Sigma) | 0.8% |
| | Ethylhexylglycerine (Seppic) | 0.2% |
| E. | Active Ingredient (oat bran polysaccharide alpha-glucans) | 4% |

Heat A and B to 80° C. Add B to A with mixing.
At 60° C. add C. Homogenize until the color is uniform.
Cool to 30° C. and add D then E.
Continue homogenizing until the make-up foundation is uniform.

Example 2

Day Cream

| A. | Water | q.s. 100% |
|---|---|---|
| | Glycerol (Univar) | 10% |
| | SATIAXANE CX 930 (Degussa) | 0.2% |
| B. | SENSANOV WR (Seppic) | 3% |
| | Phytosqualane (Sophim) | 5% |
| | Seppifeel one (Seppic) | 2% |
| | LANOL 2681(Seppic) | 5% |
| | Sophim MC 30 (Sophim) | 4% |
| | DUB PTC (Stearinerie Dubois) | 3% |
| | SEPINOV EMT10 (Seppic) | 1% |
| C. | Phenoxyethanol (Sigma) | 0.8% |
| | Ethylhexylglycerine (Seppic) | 0.2% |
| D. | Active ingredient (oat bran polysaccharide alpha-glucans) | 4% |
| E. | SIMULGEL EPG (Seppic) | 0.5% |

Heat A and B to 80° C. Add B to A with mixing.
Cool to 30° C. and add C, D and E.
Continue homogenizing until the cream is uniform.

Example 3

Transparent Fluid Serum

| A. | Water | q.s. 100% |
|---|---|---|
| | Glycerol (Univar) | 10% |
| | DUB DIOL (Stearinerie Dubois) | 10% |
| | CAPIGEL 98 (Seppic) | 4% |
| B. | Phenoxyethanol (Sigma) | 0.8% |
| | Ethylhexylglycerine (Seppic) | 0.2% |
| C. | Active ingredient (oat bran polysaccharide alpha-glucans) | 4% |
| | NaOH | q.s. pH = 6.8 |

Mix A, B and C
Adjust the pH to 6.8 with sodium hydroxide.
Continue homogenizing until the serum is uniform.

Example 4

Body Milk

| A. | Water | q.s. 100% |
|---|---|---|
| | Glycerol (Univar) | 3% |
| B. | MONTANOV 202 (Seppic) | 2% |
| | LANOL 14M (Seppic) | 1% |
| | LANOL 1688 (Seppic) | 10% |
| | DC 200 (Dow Corning) | 1% |
| C. | Ethanol | 8% |
| D. | Phenoxyethanol (Sigma) | 0.8% |
| | Ethylhexylglycerine (Seppic) | 0.2% |
| E. | Active Ingredient (oat bran polysaccharide alpha-glucans) | 4% |
| F. | Sepigel 501 (Seppic) | 2% |

Heat A and B to 80° C. Add B to A with mixing.
Cool to 30° C. and add C, D and E, then F.
Continue homogenizing until the milk is uniform.

Example 5

Facial Tensor Emulsified Gel

| A. | Water | q.s. 100% |
|---|---|---|
| | Glycerol (Univar) | 1% |
| | SATIAXANE CX 930 (Degussa) | 4% |
| B. | DC 345 (Dow Corning) | 2% |
| | Cetearyl Alcohol (Rita) | 1% |
| | MONTANOV 68 (Seppic) | 5% |
| | DUB LAHE (Stearinerie Dubois) | 5% |
| C. | Phenoxyethanol (Sigma) | 0.8% |
| | Ethylhexylglycerine (Seppic) | 0.2% |
| D. | Active ingredient (oat bran polysaccharide alpha-glucans) | 4% |

Heat A and B to 80° C. Add B to A with mixing.
Cool to 30° C. and add C then D.
Continue homogenizing until the gel is uniform.

The invention claimed is:

1. A method of providing an immediate anti-wrinkle effect and/or immediate tensor effect on the skin, comprising topically administering to a subject in need thereof an effective amount of polysaccharide alpha-glucans, wherein said polysaccharide alpha-glucans consist of oat bran polysaccharide alpha-glucans.

2. The method according to claim 1, wherein the oat bran polysaccharide alpha-glucans have a molecular weight of between 25 kDa and 300 kDa.

3. The method according to claim 1, wherein at least 90% of the oat bran polysaccharide alpha-glucans have a molecular weight of between 25 kDa and 300 kDa.

4. The method according to claim 1, wherein the oat bran polysaccharide alpha-glucans are present in a cosmetic composition, and wherein said cosmetic composition comprises between 1% and 5% by weight of the oat bran polysaccharide alpha-glucans.

5. The method according to claim 4, wherein at least 90% of the oat bran polysaccharide alpha-glucans have a molecular weight of between 25 kDa and 300 kDa.

6. The method according to claim 4, wherein the composition provides an immediate anti-wrinkle effect.

7. The method according to claim 4, wherein the composition provides an immediate cutaneous tensor effect.

8. A method of providing an immediate anti-wrinkle effect and/or immediate tensor effect on the skin, comprising topically administering to a subject in need thereof a cosmetic composition comprising
   an effective amount of polysaccharide alpha-glucans, wherein said polysaccharide alpha-glucans consist of oat bran polysaccharide alpha-glucans, and
   a dermatologically acceptable carrier.

* * * * *